United States Patent [19]

Ernst et al.

[11] 4,413,136

[45] Nov. 1, 1983

[54] PURIFICATION OF TETRAHYDROFURAN

[75] Inventors: Richard E. Ernst, Kennett Square, Pa.; Harry B. Copelin, Wilmington, Del.

[73] Assignee: E. I. Du Pont de Nemours and Company, Wilmington, Del.

[21] Appl. No.: 404,374

[22] Filed: Aug. 2, 1982

[51] Int. Cl.³ .............................................. C07D 307/08
[52] U.S. Cl. ...................................... 549/509; 549/429
[58] Field of Search ................................. 549/509, 429

[56] References Cited

U.S. PATENT DOCUMENTS

| | | | |
|---|---|---|---|
| 4,093,633 | 6/1978 | Tanabe et al. | 549/509 |
| 4,288,369 | 9/1981 | Holy et al. | 549/509 X |
| 4,348,262 | 9/1982 | Stock et al. | 549/429 X |

*Primary Examiner*—Richard Raymond

[57] ABSTRACT

The amount of methacrolein impurity in tetrahydrofuran made from acetylene and formaldehyde can be significantly reduced by treating it with hydrogen peroxide during an interval in the multi-stage distillation tetrahydrofuran refining procedure.

5 Claims, No Drawings

PURIFICATION OF TETRAHYDROFURAN

BACKGROUND OF THE INVENTION

1. Field of the Invention

This invention relates to an improvement in a process for refining crude tetrahydrofuran (THF).

2. Background Art

THF is a commodity in the chemical industry, widely used as a solvent and as an intermediate in the preparation of various polymeric glycols which are useful in preparing polyurethanes.

One of the several methods used to commercially prepare THF is a four-step process which employs acetylene and formaldehyde as starting materials. In step 1 of the process, acetylene and formaldehyde are reacted to form 1,4-butynediol, using a copper-acetylide complex as the catalyst. This reaction is described in U.S. Pat. Nos. 3,560,576 and 3,650,985, both to J. R. Kirchner.

In step 2, butynediol formed in the first step is catalytically hydrogenated to 1,4-butanediol, using Raney nickel as the catalyst. This procedure is described in British Pat. No. 1,242,358.

In step 3, butanediol from step 2 is catalytically dehydrated and cyclized to THF using sulfuric acid as the catalyst, as described in U.S. Pat. No. 3,726,905 to J. S. Coates and V. J. Reilly.

Crude THF produced in step 3 is then refined in step 4, which is a multi-stage distillation, as described in U.S. Pat. No. 4,093,633 to Tanabe, et al.

The THF produced in step 3 of the process contains methacrolein as well as dihydrofurans (2,3- and 2,5-), propionaldehyde and butyraldehydes (normal and isomeric), impurities whose presence causes color formation in polymeric glycols made from the THF. It is difficult to remove methacrolein effectively in the step 4 distillation because of the proximity of its boiling point to that of THF itself. A need therefore exists for a way of separating these impurities from THF easily and inexpensively.

SUMMARY OF THE INVENTION

It has now been found that methacrolein can readily be removed from crude THF by treating the crude THF with hydrogen peroxide and a small amount of a base.

DETAILED DESCRIPTION

The oxidation of methacrolein with hydrogen peroxide can be performed either between steps 3 and 4 as set forth above or during an interval in the step 4 multi-stage distillation and then continuing distillation.

The oxidation is carried out in a separate reactor positioned in the THF line. Hydrogen peroxide is fed into the reactor at a rate approximately equal to the amount of methacrolein present in the THF feed, since it has been found that hydrogen peroxide will destroy approximately an equal weight of methacrolein.

The hydrogen peroxide treatment is generally carried out at from 20° to 65° C. with from 25° to 45° C. being the preferred range.

The hydrogen peroxide treatment is carried out in the presence of from 10 to 100 milliequivalents per liter of THF excess of a base, with from 10-20 milliequavalents excess base per liter of THF being the preferred range. Excess base is that titrated by HCl until reaching a pH of 7.

At 35° C. and in the presence of 15 meg/liter of excess base, the methacrolein will slowly decay with a first order reaction rate of approximately 0.05 hr$^{-1}$, presumably by slow reaction with the NaOH. The addition of $H_2O_2$ to this mixture causes the very rapid (less than 30 minutes) destruction of approximately an equal weight of methacrolein.

EXAMPLE

A sample of crude THF (containing about 20% water) was spiked with about 100 ppm methacrolein. To this was added NaOH to a level corresponding to 15 milliequavalents per liter of excess caustic (that beyond the amount required to give pH 7). This sample was held at 35° C. and the methacrolein slowly decayed with a first order rate constant of 0.05 hr$^{-1}$. After 4.5 hours 13 ppm of $H_2O_2$ was added to the sample and the methacrolein level dropped in less than 30 min by about 12 ppm. Later in the experiment 26 ppm of $H_2O_2$ was added, and the methacrolein level dropped by about 40 ppm. In both cases the addition of $H_2O_2$ had little, if any, effect on the slow rate of methacrolein destruction caused by the NaOH. In a comparative experiment in which the excess caustic level was only 4 milliequivalents/liter, the methacrolein was found not to exhibit the slow decay and addition of $H_2O_2$ had no effecct on the methacrolein level.

We claim:

1. In the multi-stage refining of tetrahydrofuran made from acetylene and formaldehyde, a method of reducing the content of methacrolein impurity, which method comprises treating the tetrahydrofuran before any of the distillation stages with hydrogen peroxide in about the same weight as the methacrolein to be destroyed and from 10 to 100 milliequivalents excess of base at a temperature of from 20° to 65° C., and then separating tetrahydrofuran and the resulting chemically modified impurity.

2. The process of claim 1 wherein the base is an alkali metal hydroxide.

3. The process of claim 2 wherein the hydrogen peroxide treatment is carried out at a temperature of 25° to 45° C.

4. The process of claim 2 wherein there is from 10 to 20 milliequivalents of alkali metal hydroxide present in the hydrogen peroxide treatment step.

5. The process of claim 4 wherein the base is sodium hydroxide.

* * * * *

UNITED STATES PATENT OFFICE
CERTIFICATE OF CORRECTION

PATENT NO. : 4,413,136
DATED : November 1, 1983
INVENTOR(S) : Richard E. Ernst and Harry B. Copelin It is certified that error appears in the above-identified patent and that said Letters Patent are hereby corrected as shown below:

Column 2, line 44, before "distillation" insert --individual--.

Signed and Sealed this

Seventeenth Day of April 1984

[SEAL]

Attest:

GERALD J. MOSSINGHOFF

Attesting Officer

Commissioner of Patents and Trademarks